US006554620B1

(12) United States Patent
Iwai

(10) Patent No.: US 6,554,620 B1
(45) Date of Patent: Apr. 29, 2003

(54) AQUEOUS DISINFECTANT/STERILIZING AGENT FOR FOODS

(76) Inventor: Kazuo Iwai, 1221-1, Oaza Koshinohara, Yasu-cho, Yasu-gun, Shiga-ken (JP)

( * ) Notice: Subject to any disclaimer, the term of this patent is extended or adjusted under 35 U.S.C. 154(b) by 0 days.

(21) Appl. No.: 09/926,321

(22) PCT Filed: Sep. 28, 2000

(86) PCT No.: PCT/US00/21987

§ 371 (c)(1),
(2), (4) Date: Oct. 15, 2001

(87) PCT Pub. No.: WO02/26261

PCT Pub. Date: Apr. 4, 2002

(51) Int. Cl.$^7$ .......................... A61K 47/00; A61K 35/78
(52) U.S. Cl. ....................... 434/439; 424/725; 424/729; 424/744
(58) Field of Search .............................. 424/439, 725, 424/729, 744

(56) References Cited

U.S. PATENT DOCUMENTS

| | | | |
|---|---|---|---|
| 5,527,492 A | 6/1996 | Hayakawa | ................... 252/546 |
| 5,853,711 A | 12/1998 | Nakamura | ................ 424/78.03 |
| 5,919,398 A | 7/1999 | Nakamura | ................ 252/315.4 |
| 5,968,539 A | 10/1999 | Beerse | ........................ 424/405 |
| 6,025,312 A | * 2/2000 | Saito et al. | .................. 510/130 |
| 6,048,836 A | 4/2000 | Romano | ....................... 510/490 |

OTHER PUBLICATIONS

Database JPAP on West, No. JP 406090661, Saga et al., "Freshness–keeping material containing hinokitiol", Apr. 5, 1994, abstract.*
Database JPAB on West, No. JP406090661, Saga et al., "Freshness–keepting material containing hinokitiol", Apr. 5, 1994, abstract.

Database DWPI on West, No. 2000–066182, Kuranari et al., "Granules for preserving packaged foodstuffs–consists of granular support which carries freshness maintenance component containing iso thio organic acid, hinokitiol, bamboo extract perilla oil or tea extract" JP11318406, Nov. 24, 1999, see abstract.
Database DWPI on West, No. 1998–433192, Hayase, M. "Antibacterial insect repellent deodorised storage case–has antibacterial insect repellent deodorised chemical layer formed on inner and outer sides of case main body", JP10181776, Jul. 7, 1998, see abstract.
Abstract of Japanese Publ. No. JP11292710.
Abstract of Japanese Publ. No. JP 11281235.
Abstract of Japanese Publ. No. JP11243870.
Abstract of Japanese Publ. No. JP11228433.
Abstract of Japanese Publ. No. JP9241205.
Abstract of Japanese Publ. No. JP6263631.
Abstract of Japanese Publ. No. JP3083568.
Abstract of Japanese Publ. No. JP10036889.
Abstract of Japanese Publ. No. JP2243607.
Abstract of Japanese Publ. No. JP5271073.
Abstract of Japanese Publ. No. JP9012423.

* cited by examiner

Primary Examiner—Thurman K. Page
Assistant Examiner—Blessing Fubara

(57) ABSTRACT

The present invention provides a disinfectant/sterilizing composition which includes hinokitiol as the active ingredient. The composition has enhanced solubility of the hinokitiol in water without the need for alcohol as a solubilizing enhancing ingredient due to the presence of aloe vera extract, green tea extract, low striped bamboo extract and dokudami extract. In addition, the solubility of the hinokitiol in water is further enhanced by the additional inclusion of glycerin fatty acid ester surfactant and cara saponine emulsifier. In addition to enhancing the solubility of the hinokitiol in water, the above-noted plant extracts also serve to enhance the biocidal effect of hinokitiol and avoid the objectionable strong odor usually associated with hinokitiol compositions.

17 Claims, No Drawings

AQUEOUS DISINFECTANT/STERILIZING AGENT FOR FOODS

This application is a 371 of PCT/US00/21987 filed Sep. 28, 2000.

BACKGROUND OF THE INVENTION

1. Field of the Invention

This invention relates to the field of disinfecting or sterilizing agents. More particularly this invention is a disinfectant/sterilizing agent, which is water soluble, safe to the human body and is intended for application to perishable foods such as poultry, beef, pork and cut vegetables for killing or stopping the growth of pathogenic microorganisms to thereby disinfect or sterilize the food.

2. Description of the Related Art

Before selling meat such as chicken, beef and pork for consumption, it is necessary to stop or retard the growth of pathogenic microorganisms and it is preferable to kill pathogenic microorganisms such as bacteria or virus especially Salmonella, and *E-coli* 0-157, which may cause food poisoning due to their presence in the meat.

In order to kill or stop or retard the growth of these pathogenic bacteria or otherwise render them harmless, conventional disinfectant or sterilizing materials are used. Conventional disinfectants or sterilizing include alcohol, sodium hypo chlorite liquid, and sodium phosphate which are applied by spraying or soaking the meat in a liquid containing one or more of the above chemicals.

However, these prior art methods are not satisfactory for providing the desired disinfecting or sterilizing effect on pathogenic microorganisms such as bacteria.

For example, sodium hypo chlorite is most frequently used in tap water supply system or on other foods because sodium hypo chlorite is basically alkali and can be used with strong acid materials such as acetic acid or fruit acids to kill bacteria. However, the containers which carries these acid agents tend to rust and corrode, and due to the durability of the container and the elution of metal ions, it is difficult to utilize such agents as a food disinfectant.

Sodium phosphate has a narrow spectrum of efficacy on the bacteria and is effective in disinfecting the salmonella and coli-forms but it is not effective on *listeria* or *staphylococcus* groups of bacteria.

When alcohol is used as a disinfecting/sterilizing agent, there is the problem of residual smell of alcohol in the foods. It is rather difficult to completely remove the smell of alcohol from foods even after the food has been well rinsed with water after application. The loss of natural taste and smell associated with the use of alcohol degrades the commercial value of the food and also, the application of alcohol to certain foods is not allowed by regulation.

Hinokitiol (β-Thujaplicin) is safe to the living body, does not have the characteristics of metal corrosion, and has a wide spectrum of disinfecting/sterilizing of bacteria/virus. However, due to its low solubility in water, it is hard to make an agent which has a sufficiently high concentration of hinokitiol against the bacteria. Liquids containing a low concentration of hinokitiol is not economical cost wise, especially when consideration is given to transportation costs to transport the solution to the place of usage. Therefore it is necessary to manufacture a solution containing high concentration of hinokitiol, and dilute it at place of usage.

On this point of view, recently, in order to increase the efficacy against bacteria and to meet the requirement of accessibility, there have been a few proposals in the patent literature to concentrate hinokitiol in liquid form with combination of other ingredients. For example, the combination of hinokitiol with phenoxyethanol (in JP 2-243607) is said to have enhanced efficacy on *Pseudomonas aerginosa, Escherichia coli, Staphylococcus aureus, Bacillus subtilis, Candida albicans, Aspergillits niger* and is said to be useful for cosmetic application. JP 5-271073, discloses the combination of hinokitiol and indole, and indicates that the composition has an enhanced efficacy on *Pseudomonas aerginosa*. In JP 9-12423, a urea containing hinokitiol solution is indicated as a disinfectant, in which it is used in cosmetics such as body lotion, shampoo, and lipstick, as well as in other applications such as mouthwash as a preventive aid for *blennorrhoea alveolaris* and bad breath, and tooth paste.

However, there is no proposed usage for an aqueous hinokitiol liquid to disinfect or sterilize perishable foods by soaking or spraying directly on foods. In applying hinokitiol to foods, it is important to avoid degradation of food taste/smell. Also, because hinokitiol has a strong or stimulating odor, it is necessary to include additives to neutralize such stimulating odor or taste and to increase its water solubility. Urea or indole is unsuitable as an additive because these compounds have a strong odor and cannot be used for foods. Disinfecting agents that contain urea or alcohol are not to be used on foods due to safety considerations. These are the reasons that the above patents of hinokitiol in aqueous solution as disinfectant cannot be directly applied to foods.

An example for food application is seen in JP 9-241205. Sucrose fatty acid ester, which has a hydrophilic/lipopholic balance index of more than 17, is combined with hinokitiol for dilution in water. Sucrose fatty ester is a surface active agent and facilitates water solubility of hinokitiol. It is not forbidden to use sucrose fatty acid ester as food additive. However, when sucrose fatty acid ester is mixed with hinokitiol, it loses some of its antibacterial efficacy.

SUMMARY OF THE INVENTION

This invention solves the drawbacks of hinokitiol, which are its stimulating or strong objectionable odor and taste and difficulty of dissolving in water, and takes advantage of its safety as a food additive in perishable foods by the addition of other plant extracts.

The aqueous disinfecting/sterilizing agent of this invention is a mixture which comprises water, hinokitiol and at least one of the following extracts of aloe vera, green tea, low striped bamboo, and dokudami.

This invention provides a method of utilizing an aqueous disinfecting/sterilizing agent on perishable foods.

DESCRIPTION OF THE PREFERRED EMBODIMENT

In a preferred embodiment the invention is a disinfecting/sterilizing agent comprising hinokitiol, water and extracts of aloe vera, green tea, low striped bamboo and dokudami (houttuynia herb).

Hinokitiol, the chemical name of which is β-Thujaplicin, is contained in extracted oil of such trees as Taiwan hinoki cypress (*Chamaecyparis obtusa* var *formosana*), Aomori hiba (*Thujopsis dolabrata* var *hondai*) or incense cedar (*Calocedrus decumens*). In this invention, either natural extracted hinokitiol or synthetic hinokitiol can be used. In Japan, natural hinokitiol is approved as a food additive. For example, natural and synthetic hinokitiol are manufactured by Takasago Perfume Co., Ltd. and Osaka Organic Chemical Ind., Ltd.

Hinokitiol has a wide spectrum of efficacy on aerobic bacteria such as *Mycobacterium Tuberculosis* and *Salmonella typhosa* and anaerobic bacteria such as clostriditim and food pathogens such as Salmonella and *E-coli* 0-157. Hinokitiol has a higher efficacy than conventional food preservatives such as sodium nitrite or butyl parahydroxy benzoate and also does not generate resistant bacteria.

Hinokitiol has superior characteristics but has the disadvantage of having a distinct smell, strong taste and low water solubility. Aloe vera, green tea, low striped bamboo and dokudami (houttuynia herb) extracts are added to overcome the above disadvantages.

The amount of hinokitiol of aqueous compositions of this invention is 0.01~10% in weight. In order to maintain sterilizing efficacy against bacteria, it is preferred to keep the concentration at least 0.1%. Higher concentration of hinokitiol as an aqueous disinfectant is more desirable since it can be used by diluting with water wherever and whenever necessary. Amounts lower than 0.1% are useful for general disinfection purposes when complete sterilization is not essential such as when it is only necessary to stop or retard the growth of pathogenic microorganisms or otherwise render the microorganisms incapable of causing infection.

It has been said that the water solubility of hinokitiol as a single substance, in weight is maximum 0.2 weight %. However, in our experiment, we could not make it more than 0.1 weight %.

With this invention, by mixing hinokitiol with the extract of aloe vera, green tea, low striped bamboo and dokudami, it is possible to make a 1.0 weight % water solution without difficulty. In addition to the above mixture, we have succeeded in making 10 weight % of concentration of hinokitiol in water basis by adding glycerin fatty acid ester as surface active agent and cara saponine, which is an emulsifier. Alcohol (ethanol) is not required as an ingredient to achieve the above noted high concentration of hinokitiol.

It is known fact that with the addition of ethanol, it is possible to make 5 weight % water solution but for some foods, adding alcohol is not suitable and can change the taste of foods. Therefore, this invention of non-alcoholic water soluble disinfectant solution has particular significance.

All of the above noted extracts are well known and are commercially available.

Aloe vera extract is made from the jelly-like insides of aloe vera leaf, which is extracted by pressure and heat is added to concentrate and stabilize. In lieu of aloe extracts, aloin, which is a anthraquinone derivative or barbaroin can be used. Aloe vera extract contains aloe-emodin, aloesin, aloenin, etc. as well as, aloin and barbaroin.

Green tea extract is extracted by grinding the green tea leaves of the mature plant and combining with hot water, to produce an extract which is then refined and dried as powder. The main component of green tea is tea polyphenol. Polyphenol is a compound, which has polyphenol hydroxyl group and contains catechin, epi-catechin, gallo-catechin, epi-gallo-catechin, epi-catechin-gallerte, and epi-gallo-catechin-gallerte etc.

Extract of low striped bamboo is made by the well known method of low temperature/high pressure extraction. The extracted liquid is then concentrated. The leaves and stems of the mature plant may be used in the extraction process. Major ingredients of this concentration are triterpenoids ($\beta$-amylene and friedelin) and sugars such as residual lignin, reduction sugar and glucose. In lieu of these natural extracts, the mixture of these synthetic counterparts can be used.

Plant of dokudami (Houttuynia herb) grows naturally in Asia such as Japan, Taiwan, China, Himalayan, and Java. The extracting method is also by low temperature/high pressure method like low striped bamboo. The leaves and stems of the mature plant may be used in the extraction process. Dokudami extract contains quercitrin, afzenin, hyperin, rutin, chlorogenic acid, $\beta$-sitosterol and cis- & trans-N-(4-hydroxystyryl). In lieu of extract of low striped bamboo, the synthetic counterparts of these ingredients can be used.

Although any one of these botanical ingredients besides hinokitiol may be used as additives of this invented agent, it is preferable to use two of them and the best method is to use all four of them.

This invented agent of water based disinfecting/sterilizing agent is defined as agent containing water (preferably pure water such as deionized water) and hinokitiol and either one or two or three or all of the extracts of aloe Vera, green tea, low striped bamboo and dokudami (houttuynia herb) or its equivalent in synthetic form. When not specified, the above combination will be referred to as "aloe & other extracts" henceforth.

Ratio of these extracts contained in 1000 gram of water, hinokitiol 50 $\mu$g~100 grams, aloe vera 20 $\mu$g~100 g, green tea 20 $\mu$g~100 gram, low striped bamboo 10 $\mu$g~50 gram, dokudami 10 $\mu$g~50 gram and the ratio of these botanical ingredients except hinokitiol are determined dependent on the ingredient ratio of hinokitiol.

One embodiment of the invention contains the following ingredients: 0.05–0.2 weight % hinokitiol, 0.02–10 weight % aloe vera extract, 0.02–10 weight % green tea extract, 0.01–5 weight % low striped bamboo extract and 0.1–5 weight % dokudami (houttuynia herb) extract.

The current technology of hinokitiol water dilution ratio is 0.2% and other additives of alcohol is maximum 5%. However, this invention opens wider applications by making 10% water solution without alcohol.

In this invented agent, besides hinokitiol, aloe & other extracts, other surface active agents or emulsifiers can be added. By combining surface active agent and emulsifier, water solubility of hinokitiol increases. For example, 10% hinokitiol, 9% aloe vera extract, 8% green tea extract, 6% low striped bamboo extract, 5% dokudami extract, 1% glycerin fatty acid ester, 1% alimentary emulsifier of saponin and 60% water are mixed with a homogenizer, which is a type of agitator, for an hour at water temperature of 60–80° C. and an opalescent water based liquid is obtained.

Also in this invention, the extracts of persimmon leaf, *gynostemma pentaphyllum makino*, perilla, wasabia, madder, plum, garlic, mint, mugwort, Japanese pepper, thistle, loquat, lungwort, lavender, lemon grass, forsythia can be added. By mixing these ingredients, it neutralizes the smell or taste of hinokitiol and also it can give specific smell or taste to the agent.

In case that there is no restriction on using alcohol on certain foods, alcohol can be added to increase the solubility of hinokitiol. By adding alcohol, a high concentrate of hinokitiol containing water based disinfectant can be made.

This invented agent of water based disinfecting/sterilizing agent has wide spectrum of disinfecting/sterilizing bacteria based on the hinokitiol and does not have uncomfortable smell or taste specific to hinokitiol. When placed in mouth, it has a slight taste of mint. Therefore, it is applicable to perishable foods without losing its taste or quality. Also, since it is non-toxic, it is safe to use on foods. Higher concentration of the invented agent can be diluted at the food processing site to reduce the transportation cost. For example, in case of the average poultry plant where 10 tons of agent is required for a day, 10 kg of aqueous disinfectant of 10 weight % hinokitiol concentrate is transported and can be diluted to 100 ppm at the plant.

When using the invented agent for disinfecting food, it is preferable to apply 120~130 ppm concentration on hinokitiol basis. To make a solution containing 125 ppm of hinikitiol the following ingredients are used: Hinokitol 0.0125 weight %, aloe vera 0.11 weight %, green tea 0.105%, low striped bamboo 0.09%, dokudami (Houttuynia herb) 0.08 weight % and water (preferably pure deionized) 99.49%.

The following is the method of disinfecting the food using this agent.

The method of applying this disinfectant/sterilizing agent to food is by direct contact.

The concentration of the hinokitiol is preferably 0.05~0.2 weight %. Sterilization of food containing pathogenic bacteria which causes food toxicity, generally requires a concentration of hinokitiol of at least 0.1 wt. % to completely kill the bacteria and a higher concentration than this range may induce degradation of food quality such as in smell or taste and also effect the costs. A concentration of only 0.01 wt. % is sufficient for disinfection purposes when it is sufficient to stop or retard the growth of the bacteria without necessarily killing the bacteria to sterilize the food. A concentration of only 0.005% is sufficient to stop or retard the growth of some bacteria such as salmonella.

The methods of applying the agent to the food are as follows.

a) Showering or spraying the invented agent on foods b) Soaking the food in the invented agent within a container c) Gasify or vaporize or evaporate the invented agent in a chamber with the food d) Mix the invented agent with animal feed to kill the bacteria within the animals The foods that can be considered for sterilizing/disinfecting: vegetables such as cucumbers and leafy greens as well as pre-cut vegetables that can easily be contaminated, cooked vegetables, poultry, red meat such as beef and pork, or domestic animals prior to slaughter.

The following variables are dependent on the concentration of hinokitiol that is being used.

a) The duration time of spraying or showering b) The duration time of soaking c) The duration time of leaving the food in the chamber Under the same concentration of hinokitiol, the soaking method b of the food is the most effective because the duration time is minimum.

For example, when utilizing the aqueous disinfectant having hinokitiol 0.0125 weight %, aloe vera 0.11 weight %, green tea 0.105%, low striped bamboo 0.09%, dokudami (Houttuynia herb) 0.08 weight % and water 99.49%, a) the showering method requires more than one minute, b) the soaking method requires more than three minutes and c) gasifying, vaporizing method requires more than one hour.

In the case of the chamber method c, it is feasible to shorten the duration time to 15~30 minutes by increasing the concentration of hinokitiol to 0.1 weight %. This method is superior in processing large number or quantity of food at one time, where there is less handling of the food thus less cost in manual labor. The method of showering or spraying the agent (method a) may require less investment for equipment. Therefore, dependent upon the situation, the appropriate method can be chosen to meet the requirements.

In case of mixing in animal feed, the ratio will be dependent on the type of animal and the season, but the daily intake of hinokitiol is preferable at 5–100 ppm. For example in case of poultry feed, for 1000 kg of the feed, 0.5–1.5 kg of the invented agent in granular form which comprises extracts of hinokitiol, aloe vera, green tea, low striped bamboo, and dokudami is suggested. Daily intake of feed per chicken is approximately 100 g and the amount of hinokitiol will be 0.001% (10 ppm.)

In case of mixing the agent in animal feed, it can be mixed in as a liquid however, it is preferable to mix the agent in dry granular form. For example, the mixture of agent which contains 10 g of hinokitiol, 10 g green tea extract, 10 g aloe vera extract, 5 g low striped bamboo extract, and 3 g dokudami extract in 1 kg of water is dried by low pressure dryer so that the moisture level is down to about 10% and is in granular form. This is then mixed into the animal feed.

Because of the disinfecting/sterilizing nature of hinokitiol, the invented agent has good efficacy against wide range of pathogenic bacteria such as Salmonella, Campylobacter, *Escherichia coli* 0-157, *Staphylococcus aureus,* and *Aspergillus niger.* These bacteria which can be found in meat, fresh produce, fish and other perishable foods which are contaminated and can cause serious illness and fatalities through human consumption. Therefore, this invented agent is suitable for disinfecting/sterilizing foods.

Three disinfecting/sterilizing agents (agents I–III) are formulated as shown below in table 1.

TABLE 1

Preparation of Water Based Disinfecting/Sterilizing Agent

| Ingredients | I | II | III |
| --- | --- | --- | --- |
| Deionized water | 1000 g | 1000 g | 1000 g |
| Hinokitiol | 2 g (0.2%) | 1 g (0.1%) | *1.25 g (0.125%) |
| Aloe vera extract | 1.5 g (0.15%) | 0.75 g (0.075%) | 1.1 g (0.11%) |
| Green tea extract | 1.2 g (0.12%) | 0.6 g (0.06%) | 1.05 g (0.105%) |
| Low striped bamboo extract | 0.3 g (0.03%) | 0.15 g (0.015%) | 0.9 g (0.09%) |
| Dokudami extract | 0.3 g (0.03%) | 0.15 g (0.015%) | 0.8 g (0.08%) |

*Note:
Solution III was formulated to have 125 ppm concentration of hinokitiol (i.e., 0.125 g hinokitiol per 1000 g water). However it is not practical to measure 0.125 g hinokitiol for 1000 g water. Instead 1.25 g hinokitiol was measured for 1000 g water and diluted 10 times and this diluted solution was used to make 125 ppm concentration of hinokitiol.

Antibacterial Efficacy of the Invented Agent

By using the appropriate medium, bacteria was cultivated and bacterial growth was observed. Bacterial growth is shown by "+" and no growth is shown by "−". The tests of efficacy on various bacteria was conducted at Osaka Municipal Technical Research Institute in June~July of 1999.

Lactobacillus

Two kinds of the *lactobacillus* were tested with the invented agent type III as described above. The invented agent type III was added to peptone (0.5%), yeast extract (0.25%), glucose (0.1%), agar (1.5%) and boiled to 100° C. for 10 minutes. 20 mL each was then poured into two sterilized plates. *Lactobacillus plantarum* (IFO 3090) and *lactococcus lactis* (ATCC 11454) were transplanted onto the prepared plates and cultivated for 2 days at 30° C. and the growth of the bacteria was observed.

*Aspergillus niger*

*Aspergillus niger* (ATCC 6275) was cultivated on a potato dextrose agar plate (pH 6) at 28° C. for 7 days. Invented agent type III was added to peptone (0.5%), yeast extract (0.25%), glucose (0.1%), agar (1.5%) and boiled to 100° C. for 10 minutes. 20 mL was then poured in sterilized plates. The cultivated spores were transplanted to this plate and cultivated for 7 days at 30° C. Then, the observation of the growth of the specimen was made.

*Escherichia coli* 0-157 and *Staphylococcus aureus*

*E-coli* (IFO 3301) and *Staphylococcus aureus* (IFO 12732) were cultivated on medium composed of 0.5% of peptone, 0.25% of yeast extract, 0.1% of glucose, at pH7. The invented agent type III was added to peptone (0.5%), yeast extract (0.25%), glucose (0.1%), agar (1.5%) and boiled to 100° C. for 10 minutes. 20 mL each was then poured into two sterilized plates. In this medium, the cultivated *E-coli* and *Staphylococcus aureus* were transplanted and cultivated for 5 days at 30° C. Observation of growth of the bacteria was conducted.

Control

In place of the aqueous disinfectant, water was used and the medium for each specimen was made. The various bacteria were transplanted and the growth was observed. The results are shown in Table 2.

TABLE 2

The Result of the above Tests

| | Lactobacillus Plantarum | Lactococcus lactis | Aspergillus niger | E-Coli O-157 | Staphylococcus aureus |
|---|---|---|---|---|---|
| Invented Agent III 125 ppm Hinokitol | + | + | − | − | − |
| Control | + | + | + | + | + |

Note:
+ shows growth of the bacteria
− shows no growth.

As the results of the experiments of above, the efficacy of the invented disinfectant/sterilizing agent against *Lactobacillus plantarum* and *Lactococcus lactis* was not proven but the efficacy against *E-coli,* Staphylococcus and *Aspergillus niger* has been recognized. Since it does not kill bacteria such as Lactobacillus which are natural flora of the digestive tract, it is deemed safe and effective to give the invented disinfectant/sterilizing agent to livestock.

The Concentration of Hinokitol and Its Efficacy

The invented agent type II was used for the test. Type II agent was diluted ten times (0.1 weight % hinokitol concentration) to form agent II-A and diluted 20 times (0.005 weight % hinokitol concentration) to form agent II-B and tested for its efficacy against *E-coli* (IFO 3972) and *Aspergillus niger* (IFO 4414).

Agent II-A and II-B are combined with mediums, in which, the *E-coli* is in a standard agar and *Aspergillus niger* is in potato dextrose, separately such that they contain 3.5 weight % of the medium and are heated to 70° C. The 10 mL of standard agar and potato dextrose mediums that contain the invented agents are then poured into separate sterilized plates. The bacteria are then implanted and cultivated for 7 days at 30° C. and the growth was observed. The result are shown in Table 3 below, where growth of bacteria is shown as "+", and no growth is shown as "−".

TABLE 3

| | Hinokitiol Concentration | Elapsed days | | | | | | |
|---|---|---|---|---|---|---|---|---|
| | | 1 | 2 | 3 | 4 | 5 | 6 | 7 |
| *E-Coli* | 0.01% | − | − | − | − | − | − | − |
| | 0.005% | − | − | − | − | − | − | − |
| *Aspergillus Niger* | | | | | | | | |
| | 0.01% | − | | − | − | − | − | − |
| | 0.005% | − | | − | − | − | − | − |

Note:
+ means growth, − means no growth

It was found that even 0.005 weight % hinokitiol concentration, the invented agents inhibits the growth of bacteria for 7 days.

Efficacy Comparison Test of Hinokitiol as Single Substance and the Invented Agent

*Escherihia coli* (IFO 3972) and *Aspergillus niger* (IFO 4414) were used utilizing the minimum inhibitory method (MIC) to conduct a comparison testing the efficacy of hinokitiol as a single substance and the invented aqueous disinfectant.

Type II of the invented agent as previously described, having a hinokitiol concentration of 0.1 weight % (1000 ppm) was diluted 10 times, 20 times, 50 times, and 100 times and standard agar plate for *E-coli* and potato dextrose agar plate for *aspergillus niger* were prepared for each concentration. With hinokitiol as single substance, for 1000 g of water, 1 g of hinokitiol was used to make 0.1% solution, and this was diluted 10 times, 20 times, 50 times, and 100 times and standard agar plates and potato dextrose plates were prepared at each concentration. *E-coli* and *aspergillus niger* were implanted to the plate and cultivated for 7 days at 30° C. and the growth of the bacteria was observed. The result are shown in Table 4 below, where growth of bacteria is shown as "+", and no growth is shown as "−".

TABLE 4

| | 100 times dilution | 50 times dilution | 20 times dilution | 10 times dilution |
|---|---|---|---|---|
| Type II invented agent | | | | |
| *E-Coli* | + | + | − | − |
| *Aspergillus niger* | + | + | − | − |
| Hinokitiol | | | | |
| *E-Coli* | + | + | + | − |
| *Aspergillus niger* | + | + | + | − |

As the result are shown above, hinokitiol as a single substance is effective at 10 times dilution (hinokitiol 0.01%), however, the invented agent is effective even at 20 times dilution (hinokitiol 0.005%). This means that antibacterial efficacy is enforced by adding aloe & other extracts.

The Invented Agent Gas Chamber Exposure Test on Pathogenic Bacteria

The invented agent type I (0.2 weight % of hinokitiol based concentration) was vaporized into the airtight chamber and MRSA (methicillin resistant *staphylococcus aureus* (IFO 12732) *Escherichia coli* (IID 959), *Salmonella typhimurium* (IFO 12529) were exposed to test the antibacterial activity of the invented agent. The test was conducted at Japan Food Hygiene Association. The acrylic chamber (40 cm×40 cm×100 cm), that was used for this test, has an exhaust and an air inlet, with a vaporizer, containing the invented agent is attached to the chamber. The invented agent was vaporized through the inlet and fills the chamber. The air in the chamber is circulated for equal distribution and the temperature is held constant at 25° C. and RH (relative humidity) at 99%.

MRSA, Salmonella and E-coli 0-157 were cultivated on standard bouillon medium at 35° C. for 18 hours. Then, 0.1 mL of diluted bacteria liquid of 100 times was transplanted to a sensitivity disk medium by a platinum loop and left in the chamber which was filled with the vapor of the invented agent. After 15 minutes, 30 minutes, an hour, two hours and eight hours after the placement of the bacteria in the chamber, each time for bacteria was cultivated at 35° C. for 48 hours and the growth of each bacteria was observed. The results are shown in Table 5. In the Table 5, "+" means growth was observed, and more count of "+" means more bacteria growth. "−" means no growth. The numbers shown beneath the "+" are the actual bacterial count.

TABLE 5

| | Elapsed Time | | | | | | |
|---|---|---|---|---|---|---|---|
| | 0 min | 15 min | 30 min | 1 hr | 2 hrs | 4 hrs | 5 hrs |
| MRSA | +++ ($2.3 \times 10^5$) | ++ ($5.0 \times 10$) | − | − | − | − | − |
| E-coli | | | | | | | |
| O-157 | +++ ($4.5 \times 10^5$) | ++ ($1.3 \times 10^2$) | − | − | − | − | − |
| Salmonella | +++ ($2.1 \times 10^5$) | ++ ($2.3 \times 10^2$) | + ($8 \times 10$) | − | − | − | − |

With MRSA and E-coli, more than 30 minutes exposure, and with Salmonella, more than 1 hour to the vapor of the aqueous disinfectant can control the growth of bacteria.

Antibacterial Activity on Food

An efficacy against Salmonella on chicken meat was tested. In a container filled with the invented agent type III (0.0125weight % hinokitiol concentration), chicken carcass was soaked in the invented agent for 30 seconds, 2 minutes, and 3 minutes. The bacterial growth was compared with the control which are carcasses that were not soaked with the invented agent. Bacterial count was made using a plate in which, the cultivation medium for each bacteria are already incorporated. For Salmonella, the medium is called MLCB Agar made by Nissui Pharmaceutical. The bacteria was obtained by contacting the plate to the carcass with slight pressure and was cultivated at 37° C. and observed at 24 hours, 38 hours and 72 hours. The following Table 6 shows the test results. "+" means growth was observed, and more count of "+" means more bacteria growth. "−" means no growth.

TABLE 6

| | Cultivation Time | | |
|---|---|---|---|
| | 24 hours | 48 hours | 72 hours |
| 30 seconds soaking | − | + | + |
| 2 minutes soaking | − | − | + |
| 3 minutes soaking | − | − | − |
| Control | ++ | +++ | +++ |

The results show that the invented agent has the efficacy of controlling the growth of bacteria for 24 hours by soaking only 30 seconds. By soaking for 3 minutes, the growth of the bacteria was controlled for 72 hours.

Safety Test

Safety tests on the invented aqueous disinfecting agent were conducted for existing toxic substances, acute oral toxicity, dermal stimulation, mutagenicity, eye irritation and for standard regulatory specifications of food, regulated by the government of Japan. The invented agent concentration tested was type I (0.2 weight % hinokitiol concentration.)

a. Heavy Metal and Toxic Substance Analysis

The test for residual agricultural chemicals was conducted at Japan Food Research Laboratories, authorized institution of the government of Japan. No critical substance was detected in the invented agent.

TABLE 7

Analytical Results of the Invented Agent

| Item | Result | Limit of detection | Method of Detection |
|---|---|---|---|
| Specific Gravity (15° C.) | 1000 | | Cartesian Diver |
| pH | 10.1 | | Glass electrode |
| EPN | ND | 0.05 ppm | Gas chromatography |
| Parathion | ND | 0.05 ppm | Gas chromatography |
| Methyldimeton | ND | 0.05 ppm | Gas chromatography |
| Methylparathion | ND | 0.05 ppm | Gas chromatography |
| Arsenic as $AS_2O_3$ | ND | 0.1 ppm | DDTC-Ag absorption |
| Lead (Pb) | ND | 0.05 ppm | Atomic absorption |
| Cadmium (Cd) | ND | 0.01 ppm | Atomic absorption |
| Mercury (T-Hg) | ND | 0.01 ppm | Reduction vaporization atomic absorption |
| Tin | ND | 1 ppm | Polarography |
| Chromium | ND | 0.5 ppm | Jefenyl Calbashid |
| Cyanide | ND | 0.1 ppm | Pyridine-pyrazolone plate method | b. Regulatory Food Specifications Analysis

The invented agent type I (0.1 weight % hinokitiol concentration) was analyzed by Japan Food Research Laboratory. The result is shown in Table 8, where there were no bacteria or other metals and the liquid was transparent enough to clear the standards of soft drinks. This is based on the method of Notification No. 370, 1959 announced by the Ministry of Health and Welfare of Japan under the Specifications and Standards of Food, Additives, Etc.

TABLE 8

Standard Regulated Specifications for Soft Drinks

| Item | Result | Detection Limit | Detection method |
|---|---|---|---|
| Aerobic Plate Count | less than 30/mL | | Standard agar plate |
| Viable Mold Count | negative/1 mL | | 10% potato dextrose Standard agar plate |
| Viable Yeast Count | negative/1 mL | | 10% potato dextrose Standard agar plate |
| Standards of Soft Drinks | | | |
| Turbid | conformable | | |
| Sediment | conformable | | |
| Arsenic ($As_2O_3$) | conformable | | |
| Lead | conformable | | |
| Cadmium | conformable | | |
| Tin | conformable | 25 ppm | |
| Coliform group | conformable | | | c. Acute Oral Toxicity Study of the Invented Agent Type I in Rats

This study was conducted by Biosafety Research Center for Foods, Drugs and Pesticides, in Shizuoka, Japan.

The test was conducted on 2 males of Slc: Wistar rats (SPF) using the invented agent type I (0.2 weight % hinokitiol concentration). A Dose of 2000 mg/kg was selected and the test substance diluted with distilled water for injection directly to stomach was once administered to the animals which had fasted for 16 hours. Animals were observed the clinical signs of toxicity and mortality for 7 days after administration and measured the body weights. The pathological anatomy examinations were performed at the end of the observation period. The results are shown in Tables 9–12.

TABLE 9

Mortality

| Sex | Group | Dose level (mg/kg) | Number of Animals | Number of deaths on the day | | | | | | | Mortality (%) |
|---|---|---|---|---|---|---|---|---|---|---|---|
| | | | | 1 | 2 | 3 | 4 | 5 | 6 | 7 | |
| Male | 1 | 2000 | 2 | 0 | 0 | 0 | 0 | 0 | 0 | 0 | 0 |

$LD_{50}$ >2000 mg/kg
No mortality has been observed during the 7 day test period.

TABLE 10

Clinical Observation

Sex: Male   Dose level 2000 mg/kg   Number of animals: 2

| Signs | Hours | | | | | | | Days | | | | | |
|---|---|---|---|---|---|---|---|---|---|---|---|---|---|
| | 1 | 2 | 3 | 4 | 5 | 6 | 7 | 2 | 3 | 4 | 5 | 6 | 7 |
| Normal | 2 | 2 | 2 | 2 | 2 | 2 | 2 | 2 | 2 | 2 | 2 | 2 | 2 |
| Dead | | | | | | | | | | | | | |

Number of Affected Animals: 0   Mortality: 0/2

No abnormality has been observed in the animals.

TABLE 11

Body Weight
Weight of animals increased since an application of the invented agent.

| Group | Dose level mg/kg | Animal ID-N° | Days after administration | |
|---|---|---|---|---|
| | | | 0 | 7 |
| 1 | 2000 | 1101 | 117 g | 168 g |
| | | 1102 | 118 g | 171 g |
| | | Mean ± S.D. | 118 ± 1 g | 170 ± 2 g |

During the 7 day test period, both rats show an increase in weight after injection.

TABLE 12

Autopsy Finding

| Animal Id.-No. | Classification | Days Administration | Organ | Findings and Comments |
|---|---|---|---|---|
| 1101 | Sacrificed | 7 | | Normal |
| 1102 | Sacrificed | 7 | | Normal |

After 7 days, autopsy was made on the two animals and no abnormality was found.

As the results of the above Table 9~12, the invented agent type I has weak acute oral toxicity to rats Slc: Wistar (SPF) under the condition of this examination and $LD_{50}$ value was greater than 2,000 mg/kg of body weight.

d. Acute Dermal Irritation/Corrosion Study in Rabbit

This study was conducted by Biosafety Research Center for Foods, Drugs and Pesticides, in Shizuoka, Japan.

The test was conducted on one female of kbs: New Zealand White rabbit (healthy) using the invented agent type I (0.2 weight % hinokitiol concentration.) A flannel-patch (area in approximately 6 cm²) on which 0.5 mL of the test substance of the invented agent was spread, was applied to the left side in the back of animal for 4 hours. The animal underwent examination of dermal irritation and corrosion at 1, 24, 48, and 72 hours after treatment with the test substance. Results are shown in Table 13.

TABLE 13

Primary skin irritation in rabbit

| Animal ID-N° | Type of Treatment | Response | Time after removal of the dressing | | | |
|---|---|---|---|---|---|---|
| | | | 1 hr | 24 hrs | 48 hrs | 72 hrs |
| 2101 | Test substance | Erythema | 0 | 0 | 0 | 0 |
| | | Edema | 0 | 0 | 0 | 0 |
| | | Primary irritation index: 0.0 | | | | |

The PII (primary irritation index) is calculated by averaging the erythema values and averaging the edema values at 1 and 48 hours then combining the averages (maximum PII = 8.)

No abnormality has been observed in the treated area after 1, 24, 48 and 72 hours, therefore, the invented agent type I did not induce acute irritation or corrosion to the skin of rabbit.

e. Skin Sensitization Test in Guinea Pigs

The skin sensitization test by maximization test method was conducted at Biosafety Research Center for Foods, Drugs and Pesticides, in Shizuoka, Japan.

The test was conducted on 10 female guinea pigs of Std: Hartley strain (clean animals.) The invented agent I (0.2 weight % hinokitiol concentration) and FCA mixture was treated on the guinea pigs through intradermal injections. After one week, flannel patch (area in 2×4 cm) soaked in 0.2 mL of the invented liquid diluted by 25% pure water was applied at the upper part in the back of 5 animals for 24 hours. On the 14$^{th}$ day, after the above treatment, a flannel patch, on which 0.1 mL of the invented agent diluted with 25% distilled water was spread, was applied to the right flank of animals for 24 hours and the skin reaction was observed after 48 and 72 hours. After 48 and 72 hours, there were no reported reactions in the skin.

On the ten guinea pigs used for the test, weights of all ten guinea pigs were made before and after 25 days of the test. Result is as follows in Table 14. It is concluded that the invented agent type I did not have skin sensitization of Std:

Hartley strain guinea pigs and there was increase in their weight.

TABLE 14

| | Animal ID-No. | Body weight (grams) Before test | After 25 days |
|---|---|---|---|
| Injection Only | 2101 | 352 | 482 |
| | 2102 | 366 | 521 |
| | 2103 | 365 | 511 |
| | 2104 | 330 | 472 |
| | 2105 | 346 | 461 |
| Injection & Patching | 2201 | 397 | 526 |
| | 2202 | 367 | 552 |
| | 2203 | 347 | 485 |
| | 2204 | 345 | 448 |
| | 2205 | 299 | 502 | f. Reverse Mutation Screening Assay

By using the two strains of *Salmonella typhimurium* (TA100 & TA98), study was made on the invented agent type I (0.2% hinokitiol concentration) for reverse mutation. The test was conducted at Biosafety Research Center for Foods, Drugs and Pesticides, in Shizuoka, Japan. The results of the test are shown in Table 15 and 16.

TABLE 15

Table of Concentration Creation Test Results
Name of Test Substance: G-Clean LHB2000

| With(+) or without(−) S9 Mix | | Test substance Concentration ($\mu$g/plate) | No. of revertants (colonies/plate) | |
|---|---|---|---|---|
| | | | Base-pair substitution type TA100 | Frameshift TA98 |
| S9 Mix (31) | | Solvent control | 133 | 22 |
| | | | 128(131) | 24(23) |
| | | 8 | 122 | 21 |
| | | | 120(121) | 17(19) |
| | | 40 | 140 | 17 |
| | | | 138(139) | 18(18) |
| | | 200 | 125 | 17 |
| | | | 131(128) | 15(16) |
| | | 1000 | 114 | 21 |
| | | | 112(113) | 18(20) |
| | | 5000 | 118 | 14 |
| | | | 117(118) | 15(15) |
| S9 Mix (+) | | Solvent control | 136 | 31 |
| | | | 143(140) | 30(31) |
| | | 8 | 152 | 32 |
| | | | 143(148) | 31(32) |
| | | 40 | 153 | 28 |
| | | | 142(148) | 27(28) |
| | | 200 | 132 | 41 |
| | | | 124(128) | 40(41) |
| | | 1000 | 113 | 36 |
| | | | 113(113) | 29(33) |
| | | 5000 | 111 | 30 |
| | | | 115(113) | 27(29) |
| Positive Control | Positive control not requiring S9 mix | Name Concentration ($\mu$g/plate) Colonies/plates | AF-2 0.01 377 363(370) | AF-2 0.1 747 718(733) |
| | Positive control requiring S9 mix | Name Concentration ($\mu$g/plate) No. of colonies/plate | 2-AA 1.0 683 688(686) | 2-AA 0.5 203 196(200) |

TABLE 16

Table 16
Test Results
Name of Test Substance: The invented agent I, 2,000 ppm concentration

| With(+) or without(−) S9 mix | | Test Substance concentration ($\mu$g/plate) | No. of revertants (colonies/plate) | |
|---|---|---|---|---|
| | | | Base-pair substitution TA100 | Frameshift type TA98 |
| S9 Mix (−) | | Solvent Control | 128 | 20 |
| | | | 134(131) | 19(20) |
| | | 156 | 139 | 20 |
| | | | 137(138) | 23(22) |
| | | 313 | 134 | 23 |
| | | | 135(135) | 20(22) |
| | | 625 | 131 | 19 |
| | | | 128(130) | 18(19) |
| | | 1250 | 119 | 15 |
| | | | 127(123) | 15(15) |
| | | 2500 | 103 | 16 |
| | | | 107(105) | 16(16) |
| | | 5000 | 108 | 12 |
| | | | 102(105) | 12(12) |
| S9 Mix (+) | | Solvent control | 136 | 30 |
| | | | 130(133) | 30(30) |
| | | 156 | 133 | 30 |
| | | | 140(137) | 31(31) |
| | | 313 | 153 | 27 |
| | | | 142(148) | 31(29) |
| | | 625 | 142 | 24 |
| | | | 132(137) | 29(27) |
| | | 1250 | 118 | 31 |
| | | | 121(120) | 30(31) |
| | | 2500 | 130 | 25 |
| | | | 126(128) | 24(25) |
| | | 5000 | 110 | 36 |
| | | | 110(110) | 30(33) |
| Positive Control | Positive control not requiring S9 mix | Name Concentration ($\mu$g/plate) Colonies/plate | AF-2 0.01 408 412(410) | AF-2 0.1 698 686(692) |
| | Positive control requiring S9 mix | Name Concentration ($\mu$g/plate) Colonies/plate | 2-AA 1.0 647 650(649) | 2-AA 0.5 197 219(208) |

Counts of revertant colonies in the treated groups with type I of the invented agent (0.2% hinokitiol concentration) doses using both the direct (−S9 mix) and activation (+S9 mix) methods were comparable to those in the solvent control, that is, no increases were observed in any of the strains. No growth inhibition in the test strains was observed at any dose. Revertant colonies increased clearly in all positive controls. No remarkable change was observed during the study including the determination of colony count.

As the result, the capacity of the invented agent type I (0.2 weight % hinokitiol concentration) to induce gene mutation in bacteria was judged to be negative under the conditions of this study.

g. Inhalation Hazard Test in Rats

The test was conducted at Biosafety Research Center for Foods, Drugs and Pesticides, in Shizuoka, Japan.

Three male (7 weeks old) of Slc: Wistar (SPF) rats inhaled the test substance for 7 hours using the vaporizing chamber (W 40×D 100×H 40 cm) supplied by JCS Co., Ltd. Test substance was sprayed by the evaporative humidifier (model 3000: standard ability; 350 mL/h, Kaz Inc., USA) in the chamber. Animals inhaled the test substance for continuous 7 hours after one hour of the atomization when the evaporation density in the chamber seemed to be stabilized.

Neither food nor water was given to the animals during the exposure period. Moreover, the temperature in the chamber was 22.5–23.0° C. and humidity was 70.0–70.5% during the period of observations. Observations for clinical signs of illness were performed hourly for the first 8 hours after the beginning of the inhalation, and once daily for 7 days thereafter.

Animals were measured for body weight before inhalation and the end of the observation period. The pathological anatomy examinations were performed at the end of the observation. The result is summarized as follows.

3) Body weight (table 19)

The weight at the end of the observation has increased smoothly compared with the value just before inhalation.

1) Gross finding (table 20)
2) No abnormality was found in each animal by gross findings at the end of the observation.

It is therefore concluded that 2000 ppm (0.2 weight % hinokitiol concentration) of the invented agent did not induce any inhalation hazard to the Slc: Wistar rats. (SPF)

TABLE 17

Mortality

| Sex | Group | Number of Animals | Number of deaths on the day | | | | | | | Mortality (%) |
|---|---|---|---|---|---|---|---|---|---|---|
| | | | 1 | 2 | 3 | 4 | 5 | 6 | 7 | |
| Male | 1 | 3 | 0 | 0 | 0 | 0 | 0 | 0 | 0 | 0 |

TABLE 18

Clinical Observation

Sex: Male   Number of animals: 3

| Signs | Hours | | | | | | | | | Days | | | | | |
|---|---|---|---|---|---|---|---|---|---|---|---|---|---|---|---|
| | 1 | 2 | 3 | 4 | 5 | 6 | 7 | 8 | 24 | 2 | 3 | 4 | 5 | 6 | 7 |
| Normal | 3 | 3 | 3 | 3 | 3 | 3 | 3 | 3 | 3 | 3 | 3 | 3 | 3 | 3 | 3 |
| Dead | | | | | | | | | | | | | | | |

Number of affected animals: 0   Number of recovered animals: 0   Mortality: 0/3

In Table 17 and 18 no death or abnormality was observed in animals during the inhalation period or for 7 days after inhalation.

TABLE 19

Body weight

| Group | Animal ID No. | Days after the administration | |
|---|---|---|---|
| | | 0 | 7 |
| 1 | 1101 | 143 | 180 |
| | 1102 | 155 | 188 |
| | 1103 | 144 | 176 |
| | Mean ± S.D. | 147 ± 7 | 181 ± 6 |

Table 19 shows weight increase in the three rats during and after the exposure test.
Sex: Male
(unit: g)

TABLE 20

| Animal ID-N° | Classification | Gross finding | | |
|---|---|---|---|---|
| | | Days after Administration | Organ | Finding and comments |
| 1101 | Sacrificed | 7 | | Normal |
| 1102 | Sacrificed | 7 | | Normal |
| 1103 | Sacrificed | 7 | | Normal |

In the autopsy findings, there were no abnormality found in the three rabbits
Sex: Male c. Acute Eye Irritation/Corrosion Study on Rabbit The test utilizing the invented agent type I (0.2 weight % hinokitiol concentration) was conducted at Biosafety Research Center for Foods, Drugs and Pesticides, in Shizuoka, Japan.

The test was conducted on one female of kbs: New Zealand White rabbit (healthy.) Dose volume, 0.1 mL of the test substance was dropped into right eye of the rabbit. Non treated control was left eye. The animal underwent examination of eye irritation and corrosion at 1, 24, 48 and 78 hours after treatment with the test substance. The result of the above test is shown as follows.

TABLE 21

Primary ocular irritation scores in rabbit

| Animal ID number: | 2101 | | | |
|---|---|---|---|---|
| Time after treatment: | 1 h | 24 h | 48 h | 72 h |
| Cornea | | | | |
| A = Degree of opacity | 0 | 0 | 0 | 0 |
| B = Area of opacity | 0 | 0 | 0 | 0 |
| Score A × B × 5 | 0 | 0 | 0 | 0 |
| Iris | | | | |
| A = Values | 0 | 0 | 0 | 0 |
| Score A × 5 | 0 | 0 | 0 | 0 |

TABLE 21-continued

Primary ocular irritation scores in rabbit

| Animal ID number: | 2101 | | | |
|---|---|---|---|---|
| Time after treatment: | 1 h | 24 h | 48 h | 72 h |
| Conjunctivae | | | | |
| A = Redness | 0 | 0 | 0 | 0 |
| B = Chemosis | 0 | 0 | 0 | 0 |
| C = Discharge | 0 | 0 | 0 | 0 |
| Score(A + B + C) × 2 | 0 | 0 | 0 | 0 |
| Total score | 0 | 0 | 0 | 0 | h: hour(s)

As shown in Table 21, no abnormality was observed in cornea, iris or conjunctivae at 1, 24, 48 and 78 hours after the treatment with the test substance. It is therefore concluded that the invented agent type I did not induce acute irritation or corrosion to the eye of rabbit.

As explained previously, this invention has high efficacy in disinfecting/sterilizing bacteria and it is proved that by applying directly to the food by spraying, vaporizing or soaking the food in this invented liquid, the effect of the invention achieves its purpose without degrading food quality.

As shown in safety tests above, the invented agent is safe with regard to oral toxicity, inhalation, skin and eye irritation and has the efficacy not only against pathogenic bacteria but also, antibiotic resistant bacteria and has negative results for reverse mutation. Therefore it is environmentally safe as well.

While the present invention has been described in terms of certain preferred embodiments and exemplified with respect thereto, one skilled in the art will readily appreciate that variations, modifications, changes, omissions and substitutions may be made without departing from the spirit thereof. It is intended, therefore, that the present invention be limited solely by the scope of the following claims.

What is claimed is:

1. A disinfecting composition which comprises water, hinokitiol and either a plant extract obtained from one or more plants selected from the group consisting of aloe vera, green tea, low striped bamboo and dokudami (houttuynia herb) or a chemically manufactured equivalent of said extract and said composition does not contain ethanol.

2. The composition of claim 1 wherein said plant extract is either an extract obtained from two or more plants selected from the group consisting of aloe vera, green tea, low striped bamboo and dokudami (houttuynia herb) or a chemically manufactured equivalent of said extract.

3. The composition of claim 2 which contains more than 0.1 weight % hinokitiol up to 1 weight % hinokitiol.

4. The composition of claim 3 which contains more than 0.2 weight % hinokitiol up to 1 weight % hinokitiol.

5. The composition of claim 4 which further comprises a plant extract obtained from a plant selected from the group consisting of persimmon leaf, *gynostemma pentaphyllum makino*, perilla, wasabia, madder, plum, garlic, mint, mugwort, Japanese pepper, thistle, lowquat, lungwort, lavender, lemon grass and forsythia.

6. The composition of claim 2 which contains up to 10 weight % hinokitiol, saponin emulsifier and glycerin fatty acid ester.

7. The composition of claim 6 which further comprises a plant extract obtained from a plant selected from the group consisting of persimmon leaf, *gynostemma pentaphyllum makino*, perilla, wasabia, madder, plum, garlic, mint, mugwort, Japanese pepper, thistle, lowquat, lungwort, lavender, lemon grass and forsythia.

8. The composition of claim 6 which comprises the following ingredients per 1000 g of water:

| | |
|---|---|
| hinokitiol | 50 μg–100 g |
| aloe vera extract | 20 μg–100 g |
| green tea extract | 20 μg–100 g |
| low striped bamboo extract | 10 μg–50 g |
| dokudami (houttuynia herb) extract | 10 μg–50 g. |

9. The composition of claim 2 which comprises 0.005–0.2 weight % hinokitiol, 0.02–10 weight % aloe vera extract, 0.02–10 weight % green tea extract, 0.01–5 weight % low striped bamboo extract and 0.1–5 weight % dokudami (houttuynia herb) extract.

10. The composition of claim 6 which comprises 0.005–0.2 weight % hinokitiol, 0.02–10 weight % aloe vera extract, 0.02–10 weight % green tea extract, 0.01–5 weight % low striped bamboo extract and 0.1–5 weight % dokudami (houttuynia herb) extract.

11. The composition of claim 9 wherein said water is deionized water.

12. An animal feed additive in granular form; said animal feed additive comprising hinokitiol and either a mixture of extracts obtained from aloe vera, green tea, low striped bamboo and dokudami (houttuynia herb) or a chemically manufactured equivalent of said extract.

13. An animal feed additive in granular form, said additive made by reducing the amount of water of the composition of claim 6 an effective amount to form said animal feed additive in granular form.

14. A method for disinfecting food which comprises contacting said food with the composition of claim 9.

15. The method of claim 14 wherein said contacting is accomplished by soaking the food in said composition, spraying the food with said composition or exposing the food to the vapors of said composition.

16. The method of claim 14 wherein said food is raw poultry, beef, pork, raw vegetables or cooked vegetables.

17. A method of disinfecting the meat of an animal prior to the slaughtering thereof which comprises feeding a germicidally effective amount of the composition of claim 12 to said animal.

* * * * *

UNITED STATES PATENT AND TRADEMARK OFFICE
CERTIFICATE OF CORRECTION

PATENT NO.     : 6,554,620 B1
DATED          : April 29, 2003
INVENTOR(S)    : Kazuo Iwai It is certified that error appears in the above-identified patent and that said Letters Patent is hereby corrected as shown below:

<u>Title page,</u>
Item [73], Assignee, the assignee information should be inserted as follows:
-- Assignee: JCS Co., Ltd., Kyoto, Japan --

Signed and Sealed this

Twenty-third Day of September, 2003

JAMES E. ROGAN
*Director of the United States Patent and Trademark Office*